US009439940B2

(12) United States Patent
Orofino

(10) Patent No.: US 9,439,940 B2
(45) Date of Patent: Sep. 13, 2016

(54) TOPICAL TRANSDERMAL METHOD FOR DELIVERING NUTRIENTS THROUGH THE SKIN FOR EXPEDITIED WOUND HEALING AND SKIN REJUVENATION

(71) Applicant: Neville Pharmaceutical, Inc., Albany, NY (US)

(72) Inventor: Donald P. Orofino, Port Washington, NY (US)

(73) Assignee: Neville Pharmaceutical, Inc., Albany, NY (US)

( * ) Notice: Subject to any disclaimer, the term of this patent is extended or adjusted under 35 U.S.C. 154(b) by 0 days.

(21) Appl. No.: 13/744,072

(22) Filed: Jan. 17, 2013

(65) Prior Publication Data

US 2014/0199367 A1    Jul. 17, 2014
US 2016/0082068 A9    Mar. 24, 2016

Related U.S. Application Data

(63) Continuation-in-part of application No. 13/552,920, filed on Jul. 19, 2012.

(60) Provisional application No. 61/509,559, filed on Jul. 19, 2011.

(51) Int. Cl.

| A61K 36/886 | (2006.01) |
|---|---|
| A61K 33/34 | (2006.01) |
| A61K 33/24 | (2006.01) |
| A61K 33/06 | (2006.01) |
| A61K 31/727 | (2006.01) |
| A61K 31/664 | (2006.01) |
| A61K 31/675 | (2006.01) |
| A61K 31/455 | (2006.01) |
| A61K 31/355 | (2006.01) |
| A61K 31/201 | (2006.01) |
| A61K 45/00 | (2006.01) |
| A61M 11/00 | (2006.01) |
| A61K 45/06 | (2006.01) |
| A61K 31/198 | (2006.01) |
| A61K 31/4172 | (2006.01) |
| A61K 9/00 | (2006.01) |

(52) U.S. Cl.
CPC ........... *A61K 36/886* (2013.01); *A61K 9/0014* (2013.01); *A61K 31/198* (2013.01); *A61K 31/201* (2013.01); *A61K 31/355* (2013.01); *A61K 31/4172* (2013.01); *A61K 31/455* (2013.01); *A61K 31/664* (2013.01); *A61K 31/675* (2013.01); *A61K 31/727* (2013.01); *A61K 33/06* (2013.01); *A61K 33/24* (2013.01); *A61K 33/34* (2013.01); *A61K 45/00* (2013.01); *A61K 45/06* (2013.01); *A61M 11/00* (2013.01)

(58) Field of Classification Search
None
See application file for complete search history.

(56) References Cited

U.S. PATENT DOCUMENTS

| 4,228,153 | A  | * | 10/1980 | Burov et al. | 514/774 |
|---|---|---|---|---|---|
| 5,037,810 | A | * | 8/1991 | Saliba, Jr. | 514/56 |
| 5,652,274 | A | * | 7/1997 | Martin | 514/724 |
| 6,238,683 | B1 | * | 5/2001 | Burnett et al. | 424/405 |
| 8,012,947 | B2 | * | 9/2011 | Tomic et al. | 514/44 A |
| 8,182,840 | B2 | * | 5/2012 | Tseng et al. | 424/583 |
| 2004/0161435 | A1 | * | 8/2004 | Gupta | 424/401 |
| 2004/0175445 | A1 | * | 9/2004 | Hnat | 424/735 |
| 2004/0214749 | A1 | * | 10/2004 | Patt | 514/6 |
| 2006/0039935 | A1 | * | 2/2006 | Antosh et al. | 424/401 |
| 2007/0254853 | A1 | * | 11/2007 | Van Buren et al. | 514/44 |
| 2009/0074879 | A1 | * | 3/2009 | Braguti et al. | 424/616 |
| 2010/0310487 | A1 | * | 12/2010 | Beilfuss et al. | 424/65 |

(Continued)

FOREIGN PATENT DOCUMENTS

| GB | 2453330 | * | 4/2009 |
|---|---|---|---|
| WO | WO-93-19730 | * | 10/1993 |

(Continued)

OTHER PUBLICATIONS

Author Kali Dasa Title of publication—Valdyamanorama Page(s) being submitted—05 (p. 04-08) (Ref.p. of publication:103) Publication Date—Edn. 2005 Publisher—Central Council for Research in Ayurveda & Siddha,Govt. of India Place of Publication—New Delhi, India.

(Continued)

*Primary Examiner* — Frederick Krass
*Assistant Examiner* — Celeste A Roney
(74) *Attorney, Agent, or Firm* — Thomas A. O'Rourke; Bodner & O'Rourke, LLP

(57) ABSTRACT

The present invention relates to liquid application for skin rejuvenation created from specific amino acids, lipids, nucleic acids and vitamins. This collection of molecules delivers precisely the factors necessary to a specific site requiring healing; a direct intervention system to most expeditiously remodel skin with building blocks. This delivery is a transdermal topical delivery and healing is via specific molecules that engender a false autocoid reaction rapidly followed by an incremental healing-anti-inflammatory response augmented by very specific GRAS ingredients in the invention and also recruited from the body to this needy site. Energy is brought to site by transdermally delivered protons and enhanced by the local vascular flow initiated by transdermal molecules.

This delivery system bypasses digestion and dilution. Key is a lipophilic carrier with nuclear and mitochondrial ligands that rapidly penetrate and permeate all membranes and truncates the inflammatory site quickly manifesting curation. Other delivered molecules expedite healing at every level.

39 Claims, No Drawings

(56) References Cited

U.S. PATENT DOCUMENTS

2012/0258151 A1*  10/2012  Li et al. .................. 424/401
2013/0022687 A1*  1/2013  Fitzgerald et al. .......... 424/638

FOREIGN PATENT DOCUMENTS

| WO | WO-01-54663    | * | 8/2001  |
| WO | WO-2007-066147 | * | 6/2007  |
| WO | WO-2009-124763 | * | 10/2009 |
| WO | WO-2011-039780 | * | 4/2011  |
| WO | WO-2012-151438 | * | 11/2012 |

OTHER PUBLICATIONS

Author Mohammad Najmul Ghani Khan Title of publication—Kazaain-al-Advia vol. III (20th century AD) Page(s) being submitted—05 (p. 09-13) (Ref.p. of publication:633) Publication Date—1926 AD Publisher—Nadem Yunus Printer / Sheik Mohd Basheer & Sons Place of Publication—Lahore.

Author Ali Ibn-e-Abbaas Majoosi Title of publication—Kaamil-al-Sena'ah, Part II Page(s) being submitted—05 (p. 14-18) (Ref.p. of publication:123) Publication Date—2005 AD Publisher—Central Council for Research in Unani Medicene, 61-65 Institutional Area, Janak Puri Place of Publication—New Delhi—58, India.

* cited by examiner ated by the MN
TOPICAL TRANSDERMAL METHOD FOR DELIVERING NUTRIENTS THROUGH THE SKIN FOR EXPEDITIED WOUND HEALING AND SKIN REJUVENATION

CROSS-REFERENCE TO A RELATED APPLICATION

This application is a continuation-in-part of U.S. application Ser. No. 13/552,920, filed on Jul. 19, 2012, which claimed priority on U.S. Provisional Patent Application No. 61/509,559, filed Jul. 19, 2011, the full disclosures of which are incorporated by reference.

BACKGROUND OF THE INVENTION

Methylation is the key to the epigenetic perfect expression, peak maintenance and re-assembly of all genes (DNA/RNA). On the skin surface or wound site, methylation can be part of the energy cycle to facilitate in the epigenome's perfect retooling; the Methyl Nicotinate molecule (MN) is present to affect this reassembly on the skin surface or wound site. This process occurs without any systemic dilution or metabolic transformation that would occur by the oral or parenteral administration of the administered substance. Methyl Nicotinate molecules are lipophilic in nature and at the cellular level easily traverse through the plasma membrane. The methyl group provides energy directly to the site of application on the order of 3 protons (H+). Additional energy from increased NAD, increased NADP, increased cAMP and opening the calcium channel for increasing ATP manufacturing occurs with every molecule of MN. Once in the cytosol, it can readily enter the nucleus, delivering the Nicotinate ligand and energy. This Methyl donor energy interacts with the gene (DNA/RNA) via multiple venues; one is the histone sheath. This exposes more of the gene (DNA/RNA), now expressing its increased function and/or repair, and/or gene silencing, and/or its activation of apoptosis. The genome (DNA/RNA) is thus rebooted by the MN thereby allowing epigenetically more of the phenotypic aspects of the gene (DNA/RNA) to facilitate a renewed, reorganized and enhanced structure within the cell. The repaired gene can now perform with greater efficiency, and the repaired cell containing this gene (DNA) becomes more efficient in its innate cellular functions. There is a special energy balancing synergy to maintain perfect structure and function that requires the delicate pre-programming of the following cellular pathways: cAMP, PGC1A, Ppars, Foxo1, PARP1a, peroxisomes and proteasomes. These pathways work in synergy, aiding and contributing to optimize each individual cellular mechanism. The protons/ATP, seamlessly delivered, assist with the process of cellular respiration and maintain the balance of NAD, NADH, FAD and FADH.

Whether the gene is carrying out its normal functions or effecting self-repair, it can now do so expediently due to this delivery of energy that is both transdermally applied and systemically recruited via specific nutrients. Where RNAi or the gene has been silenced, or is malfunctioning, the increased energy delivered can retool this nuclear function. If the malfunction is not fixable, this energy can allow the cell to have PARP (parp1 in this case) induce apoptosis or autophagy via demethylization. When and if the cell rejuvenates, in turn, the energy and the nicotinate ligand for the nuclear super family of transcriptional regulated genes (NSFTRG) will induce the nucleus to engender increased production of mitochondria, proteasomic activity, Ppars, PGC1a and Sirtuin activations to continue their ever-vigilant maintenance of the gene (DNA).

Through the use of Methyl Nicotinate, the nicotinate ligand, as a promoter of the nuclear super family of transcriptionally regulated genes (NSFTRG), is attracting cytoplasmic organelles into the cytosol for increased mitochondria activity.

Within the barrier of the skin where the wound begins, the nicotinate molecule functions as a false analog, creating a false injury (an autocoid response) that is quickly recognized by the body and is quelled more rapidly than a true injury, then stimulating an anti-inflammatory healing process. The delivered beta alanine also defuses the inflammatory response allowing the anti-inflammatory response to occur more quickly.

With the absorption and transfer of the array of accompanying materials for rebuilding cellular tissue (dermis), Methyl Nicotinate causes GPRA1 activation. The event of G-protein coupled receptor A-1 activation is via skin, neurons, or immune cells release of their local free fatty acids (FFA), Phospholipase A1 (PLA1) and including arachidonic acid (AA) that recruits both the LOX cascades and COX cascades, along with a myriad of other cytokines and chemokines. (PLA1 enables AA production.) These enable local inflammation at the cell/wound site. There is also a local transformation of stem cells to mast cells with the increased production of histamine and heparin and their powerful antioxidant and anticoagulation effects at the cell site due to this local false inflammatory reaction.

Arachidonic acid by-products are legend. The body will transform AA to leukotriene via LOX interaction with AA resulting in LTA4 that hydrates to LTB4. Then glutathione helps engender LTC4 from B4. Removal of specific amino acids manifests D4 and E4 from C4. The healing cascade is as follows: B4 causes adhesion, chemotaxis and Superoxide dismutase (SOD) manufacture and, in general, invites systemic cells to come to this site to assist in a quick/short false inflammatory response. AA via COX influence produces prostanoids that have both pro-inflammatory and anti-inflammatory effect. The manufacture of PGD2 and PGE2 results in nicotinic acids vasodilatory effect that enhances local blood flow with oxygen, nutrients and cellular cleansing. PGI2 is created via COX and AA enabling an anti-inflammatory response. Both the COX and LOX truncated autocoid response enable the treated skin site to be rejuvenated. This is followed by a dedicated anti-inflammatory healing response. The addition of omega-3's: decosahexanoic acid (DHA), eicosopentanoic acid (EPA), with adjunctive acetylsalicylic acid AND the removal of MCT's and/or Emu oil enables the production of lipoxins, epilipoxins, protectins, resolvins and maresins to rapidly enhance this response by Specialized Proresolving Mediators (SPM)—autocoid production.

The nutrients delivered to the wound site with Methyl Nicotinate are specific for wound/skin healing. This action truncates inflammation and expedites the cellular healing process.

The amino acid L-Histidine is a delivered nutrient whose safety, pharmaceutical evaluation, bioavailability, physiology, metabolism, medical usage and physiologic impact are well documented in the scientific and biomedical literature. Histidine functions as a safe anti-inflammatory and antioxidant. Histidine on its own permeates the skin (integument) to reach the full dermis, down to the keritinocytes, where it renders several restorative functions. Methyl Nicotinate, described above, further enhances tissue penetration and saturation of Histidine while its redox properties allow metal cations, singlet oxygen and hydroxyl groups to be reduced and/or neutralized, and rendered non-toxic. Free Histidine (HD) is found in all tissue. As HD is decarboxylated to histamine (HA), beta-alanine can combine with HA in the presence of carcinine synthetase forming carcinine (CA). Alternately, HD may combine with beta-alanine, in the presence of carnosine synthetase, to become carnosine.

Carnosine (CS) is important in protein manufacturing and diminishing glycosylation and carbonylation. By the modes of actions of HA/HD/CS/CA cells may restore their intrinsic resting electrical potential. This energizing effect further creates within the epidermal and subdermal layers of the skin the re-scaffolding needed for new tissue formation and for the building from connective tissues using CS, an integral component, along with glycine and imidizole acetic acid (IAA), which are needed to provide for the collagen and elastin formation.

While in the re-scaffolding process, reactive oxygen species (ROS) and nitric oxide synthase (NOS) need suitable blockade occurring via the HD, HA, CA and CS molecules that prevents the oxidative deterioration and weakening of the newly formed scaffolding. In fact, all the nutrients and molecules being delivered to skin/wound have an increased shelf life because of these antioxidant molecules. Quintessentially, HD opens the aquaporine channels (AQP0). Specifically, aquaporine increases the PH within the cell as a signaling mechanism and turns on the calcium channel-signaling pathway (nicotinic acid assisted) that provides cellular hydration directly through aquaglyceroporin channels, as well as a milieu to enhance cellular respiration and increase energy manufacturing. Induced Carcinine (CA): HA, derived from HD, can be biochemically changed to CA via HA combining with beta alanine and P-5-P in the presence of Carcinine synthase. CA is an analog of CS. Although CA is best produced in the central nervous system (CNS) at a rate of 15-fold greater saturation than found in any other tissue, its mode of action for healing is mainly seen through the cardiovascular system. The Epiphenomenon permits CS and CA to work directly to influence an increased blood flow and cardiac output to heal injured tissues. Deep tissue (muscle and fascia) restoration relates to CS presence that is essential with deep wound healing. CA directly decreases and/or reverses skin aging. The transdermal mechanism allows application and delivery to the exact area of injury of HD, HA, MN, CS, CA, amino acetic acid (AAA), IAA, glycine, P-5-P, Copper (Cu++), and the medium chain triglycerides (MCT) molecules that the integument requires for repair. These restorative nutrient components are either applied to the site of repair or are biochemically and/or physiologically produced in situ or alternatively delivered to the site by locally increased circulation and/or local neurologic discharge.

Additional concentrations of HA and HD pool at injury sites acutely by proximal neural firing. This effects increased HD and HA locally. HA and HD may then be oxidized along with beta alanine to amino acetic acid, and/or imidazole acetic acid (IAA), and/or they can be methylated. Pain at the N-Methyl D-Aspartate (NMDA) sites may be mitigated by IAA occupying the glycine receptor adjacent to the glutamate site. HD is ubiquitous and creates special prostaglandins of the 2 series (PGE2) at the inflammatory sites, which assist in creating accelerated tissue growth. HD and HA, with their bio-degratory amino acetic acids (AAA) are integral in nucleic acid production, essential for new cell growth and replenishment.

Energy for healing is essential. Methyl Nicotinate, a nicotinic acid (B3) with a methyl group attached for its lipophilicity, transports and transfers energy locally. Nicotinate increases the surface temperature of the skin (warming) and causes a significant release of prostaglandins (PGE 2) from the skin. It stimulates histamine release from mast cells in the tissue, thereby initiating the autacoid response of the specific immune system. Methyl Nicotinate, a forerunner of NADPH and NADH are the keys in glucose metabolism. They are required for the energy production needed for healing. This action is accomplished through the donation of an electron, resulting in increased energy for rapid and repeatable cellular tissue repair.

Methyl nicotinate synergizes with pyridoxal-5-phosphate (P-5-P) and Cu++ to promote scaffolding for the collagen/elastin infrastructure and to efficiently reassemble "big" collagen (potential scarring) to normal collagen. The direct infusion of Cu++ increases skin growth and matrix molecules for faster keritinocyte growth, thereby yielding faster dermal growth. P-5-P with nicotinic acid are necessary for keritinocyte and skin regrowth, as PARP and Sirtuins both require NAD as an essential substrate. They enable new undamaged dermal regrowth. Including both MN and NA in this formula promotes a two-pronged both "time release" effect on energy enhancement required for new skin generation via NAD, cAMP, cytosolic Ca++ regulation, increased efficiency of CAC with diminished ROS.

Pyridoxal-5-phosphate (P-5-P) with MN assists in energy production, and in wound/skin methylation by direct application to the site of injury. Like Methyl nicotinate it bypasses per oral digestion and systemic dilution, locally empowering this wound/skin site to grow and heal more rapidly than normal. P-5-P directly facilitates copper in the proper redox state to avoid toxicity, thereby increasing the reactive oxygen species (ROS) being neutralized. The increased bioavailability of the vitamin C for tissue factors (e.g. Glycosaminoglycan) is enhanced by healthy copper at the wound site. P-5-P is a critical factor for the supply of energy, materials and preparation required for on site healing.

Ceramide manufacture, engendered by niacin, increases skin production along with signaling molecules for apoptosis, cell growth and/or cell differentiation.

Medium Chain Triglycerides (MCT's) are structured lipids C-6 through C-12 that are applied topically to the wound to assist in energy, cell wall manufacture and healing.

Heat Shock Proteins (HSP). The induced local inflammatory site engenders heat shock proteins (HSP) to assist in the chaperoning of specific molecules to their necessary destination of skin and soft tissue remanufacturing sites. Additionally, heat shock factors (HSF1) partner in this same process.

Ribosome switches, or Ribo switches, are now recognized as one of the major metabolite controlling systems that account for about two percent (2%) of genetic regulation in bacteria. They respond to various metabolites, including co-enzymes, sugars, nucleotide bases, amino acids and cations. With Thiamine, Methyl donor groups, glycine and B-alanine, the ribo-like switches can be turned on, off and incrementally speed up the healing of skin/wounds, bypassing part of the molecular networking that could impede this process.

Sirtuins are necessarily activated by the upstream and downstream energy circuitry that is engendered by multiple networking molecules (CREB, CREM, cAMP, FOXO1, FOXO3a, PPARS, and PGC1a). PGC1a becomes a special additional immediate fuel source for SIRTS by its manifold acetylated lysines. This entire energy loop is the source for wound healing. The above is engendered in part or all by the methylation process and redox upregulation by Methyl Nicotinate, P-5-P, Cu++ and Inosine (a nucleoside).

Inosine is a necessary precursor of cellular energy and efficiency. It sustains cellular and extra cellular ATP for integument maintenance and growth. In new skin formation it enables oxygenation and new ATP manufacture essential for growth. Its neuro protectant application is essential for preservation and regrowth of neural tissue in the healing wound. Inosine is commonly found in tRNA that impacts on RNA editing and RNAi for maximal cellular integrity.

Additional transdermal nutrient delivery molecules in this invention that augment efficacy and potency of this invention are (1-5):

1. ALA (alpha lipoic acid) a thiol and antioxidant that interacts with lipid and water-soluble antioxidants increases peak longevity of these several nutrients. ALA reboots vitamin C, vitamin E, ubiquinone and glutathione thereby reducing ROS yet increasing local nutrient bioavailability. ALA architecturally undergirds new dermal growth with glycine and imidizole acetic acid (IAA) allowing dermal structure to emerge under the scrutiny of a genetic cleavage system (caspase proteases) under the protection of the above antioxidants. It also increases eNOS (endothelial nitric oxide synthase) and increases nitric oxide vasodilation.
2. Beta-alanine, above biochemically discussed and applied in earlier text here, is key to the remodeling of injured, diseased or aged skin, suppresses leukotriene (LT) especially LT (B4) thereby diminishing the circadia of the false inflammatory autocoid response of methyl nicotinate (MN) and thus more rapidly engenders an anti-inflammatory healing response.
3. Glycerol, propylene glycol and polysorbate 20 allow more efficient transdermal penetration of molecular substrate. These hydroscopic nutrients with medium chain triglycerides (MCT's) enable enhanced dermal permeation and therefore expedited dermal regrowth.
4. Thiamine enables pyruvate dehydrogenase activity to increase by energizing all cellular rejuvenatory capacity via the CAC cycle and thus defusing neuropathy, myopathy, vasculopathy and endocrinopathy.
5. Riboflavin, in addition to its manifold attributes, provides the litmus test of transdermal penetration of this invention by the increased yellow intensity of the urine as absorption crescendos and later decrescendos. It visually depicts the transdermal invention as it transits through your body.

All of these nutrients, whether supplied transdermally or recruited to the site, play an important role in the accelerated healing and/or rejuvenation that takes place with this unique formulation and delivery system.

Aquaporins ("AQPs") constitute a major conduit for movement of water across plasma membranes. AQP0 is expressed in the fiber cells. AQP0, engendered by Histidine, is critical for cell homeostasis. Several cellular functions have been attributed to AQP0. In vitro and ex vivo experiments have confirmed the water permeability function of AQP0. It is my belief that AQP0 performs cell-to-cell adhesion. There is strong support and empirical data validating the possible structural role of AQP0 as a cell-to-cell adhesion protein influencing subdermal ceramides.

BRIEF SUMMARY OF THE INVENTION

The present invention relates to therapeutic composition that is comprised of a blend of active and inactive ingredients that includes specific and highly selective proteins, amino acids, and nucleic acid molecules. This therapeutic composition has sequences encoding such proteins, nutrient catalyzing cofactors, antibodies and short antisense-like molecules existing and innate within the sub dermal layer. Also included in the present invention are specific functional methods to enable and utilize such polypeptides to modulate healing, apoptosis, riboswitch-like activation and curation of wounds. The active ingredients are all GRAS ("generally regarded as safe") and all natural. They are factors in the apoptotic cascade, and in the control and modulation of said bodily processes specifically present for the purpose of wound curation and truncation of the insult/injury cycle. The inherent synergy between components provides for an internal milieu that utilizes the body's own recovery cycle and the antisense-like technology underscored by this invention. The present invention provides a time-staged delivery of beneficial nutrients transdermally through the medium of a methyl carrier for the purpose of cellular remodeling, as well as cleavage by a variety of different caspase proteases that are capable of inhibiting apoptosis. The amount of nutrients delivered may depend on a variety of factors, including the molecular size of the nutrients, the solubility of the nutrients, the condition of the skin that is being treated, the ambient temperature, the medical condition of the patient, and whether any other medications or skin ointments are also being taken by the patient.

Mitogen-activated protein kinase kinase kinase 1 is an enzyme that in humans is encoded by the MAP3K1 gene. MAP3K, or MEK kinase, is a serine/threonine kinase that occupies a pivotal role in a network of phosphorylating enzymes integrating cellular responses to a number of mitogenic and metabolic stimuli, including insulin and many growth factors. Mouse genetics has revealed that the kinase is important in correct embryogenesis, keratinocyte migration, T cell cytokine production and B cell antibody production.

DETAILED DESCRIPTION OF INVENTION

I have discovered that a variety of nutrients (i.e. vitamins, trace minerals, fats and select amino acids) delivered transdermally/topically in a staged and sequential manner, through the conveyance of a methyl carrier, i.e., a carrier for the methyl group which can preferably be methyl nicotinate, provide a meaningful, measurable and significant way to both induce and transport these active healing substances. This combination of nutrients, such as amino acids and mineral cofactors, function as a therapeutic composition and enables the body's own healing and innate immune system to recreate a healed dermis now in homeostasis.

2. The components of the therapeutic composition include but are not limited to alpha and gamma tocopherols, B-complex vitamins. Preferably, the composition includes nicotinic acid, the amino acids glycine and histidine, histamine, beta-alanine and taurine, copper and magnesium, P-5-P, polysorbate 20, glycerol, medium chain triglycerides, glycerophosphocholine ("gpc"), propylene glycol, oleic acid, MN, Inosine, and water.

Representative Formulation of Ingredients—Percent & Volume

The therapeutic composition of the present invention preferably comprises at least one active ingredient component and at least one inactive ingredient component. The composition is also preferably a solution that includes as an active component a methyl nicotinate component in an amount of about 0.1% to about 1.0%, more preferably from 0.2% to 0.8%, and most preferably from 0.25% to 0.5%. There can be additional active components. These active components can preferably include one or more of the following:

| | |
|---|---|
| Arachidonic Acid | ~0-~3%, preferably 0.25%-2.5%, more preferably 0.5%-2.0%, and most preferably 0.75%-1.5% |
| Amino Acidic Acid | ~0-~5%, preferably 0.5%-4.5%, more preferably 1.0%-4.0%, and most preferably 1.75%-3.5% |
| Histidine | ~0-~8%, preferably 1.5%-7.25%, more preferably 3.0%-6.0%, and most preferably 4.5%-5.5% |
| Copper Peptide | ~0-~5%, preferably 0.5%-4.5%, more preferably 1.0%-4.0%, and most preferably 1.75%-3.5% |
| Ascorbyl Palmitate | ~0-~3%, preferably 0.25%-2.5%, more preferably 0.5%-2.0%, and most preferably 0.75%-1.5% |
| Niacinamide/ Nicotinic Acid | ~0-~3%, preferably 0.1%-2.5%, more preferably 0.3%-2.0%, and most preferably 0.4%-1.5% |
| Histamine | ~0-~5%, preferably 0.5%-4.5%, more preferably 1.0%-4.0%, and most preferably 1.75%-3.5% |
| Beta Alanine | ~0-~4%, preferably 0.5%-3.5%, more preferably 1.0%-3.0%, and most preferably 1.5%-2.5% |
| Hypoxanthine Riboside | ~0-~2%, preferably 0.25%-1.75%, more preferably 0.5%-1.5%, and most preferably 0.75%-1.25% |
| Mixed Tocopherols (Vitamin E) | ~0-~2%, preferably 0.25%-1.75%, more preferably 0.5%-1.5%, and most preferably 0.75%-1.25% |
| P-5-P | ~0-~5%, preferably 0.5%-4.5%, more preferably 1.0%-4.0%, and most preferably 1.75%-3.5% |
| Glycine | ~0-~2%, preferably 0.1%-1.75%, more preferably 0.3%-1.5%, and most preferably 0.4%-1.25% |
| Taurine | ~0-~2%, preferably 0.25%-1.75%, more preferably 0.5%-1.5%, and most preferably 0.75%-1.25% |

Conditional Ingredients that may be used include Alpha Lipoic Acid, Carnosine, and Inosine. The amount of conditional ingredients used may range from about 0% to about 5% of the therapeutic composition. Preferably, the amount of conditional ingredients may range from 0.01% to 2%. However, for wound care applications, the amount of conditional ingredients may preferably range from 0.1% to 5%.

In addition to the active components there is preferably at least one inactive component in the composition. The inactive component can include one or more of the following:

| | |
|---|---|
| Glycerol | ~0-~2%, preferably 0.1%-1.75%, more preferably 0.3%-1.5%, and most preferably 0.4%-1.25% |
| Caprylic/Caprylate Triglycerides (MCT) | ~0-~3%, preferably 0.5%-2.75%, more preferably 1.0%-2.5%, and most preferably 1.5%-2.25% |
| Polysorbate 20 | ~0-~1%, preferably 0.1%-0.9%, more preferably 0.2%-0.8%, and most preferably 0.3%-0.7% (sufficient to mix oils/H20 to give emulsion): preferred is a natural source such as coconut |
| Propylene Glycol | ~0%-~15%, preferably 0.1%-13.75%, more preferably 0.2%-12.5%, and most preferably 0.3%-11.25% (solvent in cosmetics) |
| Phosphatidylcholine | ~0-~3%, preferably 0.25%-2.5%, more preferably 0.5%-2.0%, and most preferably 0.75%-1.5% |
| Lysophosphatidylcholine | ~0-~0.1%, preferably 0.005%-0.075%, more preferably 0.01%-0.05%, and most preferably 0.015%-0.05% |
| Ethanol | an amount sufficient to pass a Micro biological Assay test |
| Glyceryl Stearate | ~0-~1% (emulsifier), preferably 0.1%-0.9%, more preferably 0.2%-0.8%, and most preferably 0.3%-0.7% |
| Oleic Acid | (sufficient to pass thru the dermis only) |
| Tetrasodium EDTA (stabilizer) | 50-200 ppm (≤2% by weight) preferably 70-180 ppm, more preferably 90-160 ppm, and most preferably 110-140 ppm |
| Deionized Water | balance of solution |

An example of a preferred composition is as follows wherein the ingredients are in the form volume percent:

| Active Ingredients (~26.5%-~27%) | |
|---|---|
| Methyl Nicotinate | ~0.25%-~1% |
| Arachidonic Acid | ~1% |
| Amino Acidic Acid | ~3% |
| Histidine | ~5% |
| Copper Peptide | ~3% |
| Ascorbyl Palmitate | ~1% |
| Niacinamide/Nicotinic Acid | ~0.5%-~1% |
| Histamine | ~3% |
| Beta Alanine | ~2% |
| Hypoxanthine Riboside | ~1% |
| Mixed Tocopherols (Vitamin E) | ~1% |
| P5P | ~3% |
| Glycine | ~0.5%-~1% |
| Taurine | ~1% |

| Conditional Ingredients | |
|---|---|
| Alpha Lipoic Acid, Carnosine, and/or Inosine | ~1%, or increase to ~3% for wound care only |

| Inactive Ingredients | |
|---|---|
| Deionized Water | balance of solution |
| Glycerol | ~0.5%-~1% |
| Caprylic/Caprylate Triglycerides (MCT) | ~2% |
| Polysorbate 20 | ~0.5% (sufficient to mix oils/H20 to give emulsion), e.g. natural source coconut |
| Propylene Glycol | ~0.5%-~10% max (solvent in cosmetics) |
| Phosphatidylcholine | ~1% |
| Lysophosphatidylcholine | ~0.02% |
| Ethanol | an amount sufficient to pass Micro biological Assay test |
| Glyceryl Stearate | ~0.5% (emulsifier) |
| Oleic Acid | sufficient to pass thru the dermis only |
| Tetrasodium EDTA (stabilizer) | 50-200 ppm (≤2% by weight) |

Water is the overall solvent for many of the ingredients, but to formulate the spray most effectively water and fat-soluble emulsions must be homogenized for best transdermal bioavailability and application.

The components of this mixture are used in a combination in range used to treat non-medical as well as medical conditions. Topical and/or transdermal treatment is preferred for local control of disease states and inflammatory cascade states to insure that any disapparate and/or unwanted side effects are minimized and curtailed.

Varieties or combinations of this therapy include, though are not limited to the following:
  (a) A topical/transdermal spray using a radiating pump dispenser;
  (b) A topical/transdermal salve/balm rubbed into the skin;
  (c) A topical/transdermal gel w/*aloe vera* and vitamin E rubbed into the skin;
  (d) A topical/transdermal wound/burn cleansing rinse;
  (e) A topical/transdermal roll-on for pain relief;
  (f) An impregnated mini-sponge individually hermetically sealed with said composition that can be reconstituted with water;
  (g) A wound powder composed of micronized, freeze dried material used for pressure ulcers and diabetic wounds, and
  (h) A time-released epidermal/topical patch for staged and sequential delivery of said composition for site-specific application.

The therapeutic composition may preferably be administered about 1-4 times per day on a daily basis until the wound is healed as desired and/or the skin rejuvenated as desired. In addition, the therapeutic composition may alternatively be administered on a bi-weekly, tri-weekly, weekly or monthly basis until the wound is healed as desired and/or the skin rejuvenated as desired. Furthermore, the administration may initially begin on a daily basis and then, in response to clinical improvement, transition to a weekly, monthly, etc. administration. Rather than being used solely as a treatment aid, the composition of the present invention may also be used to maintain a user's skin in good condition.

The most convenient method of applying the compound is to spray the compound on the desired site of a user's skin with no covering or other compounds applied to the location. It is preferable to leave the compound exposed to air for 15 to 30 minutes after having been applied to the skin. An osmotic/absorptive gradient can wean the composition from the skin to the dressing, thereby depriving composition content from the needy delivery site. Wound cover can be applied as clinically required.

What is claimed is:

1. A method of supplying a therapeutic agent locally to a wound site on a body of a patient,
  wherein said method comprises applying said therapeutic agent transdermally to tissue at said wound site to promote healing at the wound site;
  wherein said therapeutic agent comprises a homogenized blend of a carrier and a treatment agent;
  wherein said carrier comprises methyl nicotinate and beta-alanine, said methyl nicotinate delivers energy to said wound site by delivering protons to said wound site, said energy provided by said protons allows for self-repair at said wound site, said beta-alanine accelerates the inflammatory response of the patient's body to allow the anti-inflammatory response of the patient's body to occur more quickly and promote the healing at said wound site;
  wherein said blend also comprises histidine, glycine, taurine, hypoxanthine riboside, thiamine, pyridoxal-5-phosphate, alpha-tocopherol, gamma-tocopherol, and copper in the form of $Cu^{++}$;
  wherein said hypoxanthine riboside acts as a precursor of cellular energy and, together with said methyl nicotinate, said pyridoxal-5-phosphate, and said copper, facilitates methylation and redox upregulation; and
  wherein said glycine, said thiamine, and said beta-alanine activate ribosome switches to speed up healing at said wound site.

2. The method according to claim 1, wherein said blend also contains at least one ingredient selected from the group consisting of imidazole acetic acid, nicotinic acid and carnosine.

3. The method according to claim 1, wherein said blend includes a solvent consisting of a mixture of water and ethanol.

4. The method according to claim 1, wherein said blend includes from 0.1 to 0.9% of glyceryl stearate in order to facilitate emulsifying said blend.

5. The method according to claim 1, wherein said blend includes ≥2 wt. % of ethylene-diaminetetracetic acid (EDTA) in order to stabilize said blend.

6. The method according to claim 1, wherein said blend also includes from 0.5% to 4.5% of histamine, from 0.1 to 2.5% of nicotinic acid and/or niacinamide, from 0.1 to 2% of alpha-lipoic acid, from 0.1 to 2% of carnosine, and from 0.25 to 2.5% of ascorbyl palmitate.

7. The method according to claim 1, wherein said blend also includes from 0.25 to 2.5% of phosphotidylcholine and from 0.01% to 0.05 of lysophosphatidyl choline.

8. The method according to claim 1, wherein said blend also contains from about 0.1 to about 1.0% of said methyl nicotinate, from 0.25 to 2.5% of arachidonic acid, from 0.25 to 1.75% of said hypoxanthine riboside, from 3 to 7.25% of said histidine, from 0.1 to 1.75% of said glycine, from 0.5 to 3.5% of said beta-alanine, from 0.25 to 1.75% of said taurine, from 0.25 to 1.75% of said alpha and gamma tocopherol and from 0.5 to 4.5% of said pyridoxal-5-phosphate.

9. The method according to claim 1, wherein said blend includes inactive ingredients and wherein said inactive ingredients comprise deionized water, ethanol, glycerol, caprylic/capriliate triglycerides, polysorbate 20, propylene glycol, at least one emulsifier, and at least one stabilizer.

10. The method according to claim 1, wherein said blend includes at least one copper peptide in order to supply said copper.

11. The method according to claim 1, wherein said blend also includes histamine.

12. The method according to claim 1, wherein said blend further comprises magnesium.

13. The method according to claim 1, wherein the blend further comprises an excipient.

14. The method according to claim 13, wherein the excipient is polysorbate 20.

15. The method according to claim 1, wherein said blend further comprises glycerol or at least one derivative thereof.

16. The method according to claim 15, wherein the derivative of said glycerol is a medium chain triglyceride.

17. The method according to claim 16, wherein the triglyceride is a caprylic or caprylate triglyceride.

18. The method according to claim 15, wherein the derivative of said glycerol is glycerophosphocholine.

19. The method according to claim 1, wherein the blend further comprises a solvent.

20. The method according to claim 19, wherein said solvent is at least one ingredient selected from the group consisting of water, ethanol, glycerol and propylene glycol.

21. The method according to claim 1, wherein the blend is applied using a radiating pump dispenser.

22. The method according to claim 1, wherein the blend is applied as a salve or balm rubbed into the skin.

23. The method according to claim 1, wherein the blend is a gel.

24. The method according to claim 23, wherein said blend further comprises aloe vera.

25. The method according to claim 1, wherein said blend is applied as a wound cleansing rinse.

26. The method according to claim 1, wherein said blend is applied as a burn cleansing rinse.

27. The method according to claim 1, wherein said blend is packaged in an individually hermetically sealed package and wherein said blend has been dehydrated and can be reconstituted with water.

28. The method according to claim 1, wherein said blend is applied as a powder comprised of micronized, freeze dried material.

29. The method according to claim 28, wherein said blend treats pressure ulcers.

30. The method according to claim 28, wherein said blend treats diabetic wounds.

31. The method according to claim 1, wherein said blend is applied by a time-released epidermal or topical patch for staged and sequential delivery of said composition for site-specific application.

32. The method according to claim 1, wherein the treatment agent further comprises an anticoagulant.

33. The method according to claim 32, wherein said anticoagulant is heparin.

34. The method according to claim 1, wherein the treatment agent is applied to keratinocytes and causes accelerated new dermal growth.

35. The method according to claim 1, wherein the carrier further comprises a 0.5 to 5% of a copper peptide.

36. The method according to claim 1, wherein the carrier further comprises niacinamide.

37. The method according to claim 1, wherein the carrier further comprises nicotinic acid.

38. The method according to claim 1, wherein said blend is applied by a roll on applicator.

39. The method according to claim 1, wherein said blend is applied by a blend impregnated mini-sponge.

* * * * *